United States Patent [19]

Ashby

[11] 4,421,903

[45] Dec. 20, 1983

[54] PLATINUM COMPLEX CATALYSTS

[75] Inventor: Bruce A. Ashby, Schenectady, N.Y.

[73] Assignee: General Electric Company, Waterford, N.Y.

[21] Appl. No.: 352,522

[22] Filed: Feb. 26, 1982

[51] Int. Cl.³ ............................................. B01J 31/02
[52] U.S. Cl. ...................................... 528/15; 502/158; 502/169
[58] Field of Search ...................... 252/431 R, 429 R; 528/15

[56] References Cited

U.S. PATENT DOCUMENTS

| | | | |
|---|---|---|---|
| 3,159,601 | 12/1964 | Ashby | 260/46.5 |
| 3,159,662 | 12/1964 | Ashby | 260/448.2 |
| 3,383,356 | 5/1968 | Nielsen | 260/46.5 |
| 3,419,593 | 12/1968 | Willing | 260/448.2 |
| 3,775,452 | 11/1973 | Karstedt | 260/429 R |
| 3,814,730 | 6/1974 | Karstedt | 260/46.5 |
| 4,288,345 | 9/1981 | Ashby et al. | 252/431 R |

*Primary Examiner*—Patrick Garvin
*Attorney, Agent, or Firm*—Hedman, Casella, Gibson, Costigan & Hoare

[57] ABSTRACT

Platinum complexes of unsaturated siloxanes, substantially free of inhibitory compounds, provide superior hydrosilation catalysts when produced by heating a platinum compound with an unsaturated siloxane of the formula

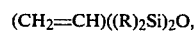

$(CH_2=CH)((R)_2Si)_2O$, wherein R is free of aliphatic unsaturation and is selected from alkyl, cycloalkyl, and aryl groups, the amount of siloxane being selected to provide not less than about 0.01 gram atom of platinum per mole of vinyl content, and a platinum content of not less than about 2 percent by weight in the catalyst. Curable silicone compositions containing such catalysts are also provided.

10 Claims, No Drawings

PLATINUM COMPLEX CATALYSTS

The present invention relates to novel compositions for catalyzing the reaction of hydrogen-bonded silanes or siloxanes with aliphatically unsaturated and/or hydroxyl-containing organic compounds, especially aliphatically unsaturated and/or hydroxyl-containing organopolysiloxane compounds.

BACKGROUND OF THE INVENTION

In Willing, U.S. Pat. No. 3,419,593, in Karstedt, U.S. Pat. No. 3,814,730, and in Ashby and Modic, U.S. Pat. No. 4,288,345, are described complex catalysts comprised of platinum and unsaturated siloxanes, and their use in the so-called hydrosilation reaction between compounds containing silicon-bonded hydrogen and aliphatically unsaturated organic compounds, especially aliphatically unsaturated organopolysiloxane compounds. It is also known to use such catalysts in the reaction of organosilanol compounds with hydrogenosiloxanes to produce a new siloxane and hydrogen gas. Curable compositions useful as encapsulants for electronic components, and the like, comprise organopolysiloxanes having at least two aliphatically unsaturated groups or at least two silicon-bonded hydroxyl groups, a silicon hydride, and such platinum complex catalysts and these can be provided in foamable modifications, as well as filled modifications, containing e.g., from 10 to 300 parts of filler per 100 parts of organopolysiloxane. The disclosures of the above-mentioned patents are incorporated herein by reference, and the latter-mentioned ones as well.

The Willing patent describes, typically, the heating together of symmetrical divinyltetramethyldisiloxane in large excess with chloroplatinic acid then cooling, diluting with still more of the disiloxane, filtering and then washing with water to remove acidity. Adding trace amounts of this composition to a mixture of a polyhydrogenmethylsiloxane and a vinyl-containing polydimethylsiloxane, followed by gentle heating produces a gel, indicating that the known reaction between the $\equiv$SiH and CH$_2$=C— linkages has taken place.

Karstedt discloses that superior catalysts can be formed if pains are taken to remove all, or substantially all, of the inorganic halogen which is produced in the reaction between a platinum halide and an unsaturated siloxane. The use of an acid-binding agent like sodium bicarbonate is specified to remove inorganic halogen before the platinum-siloxane complex is used as a catalyst.

Catalysts prepared by the Willing and Karstedt methods have been found to be somewhat less than satisfactory in terms of rate of cure, for example, because they contain numerous intermediate structures and they appear to be encumbered by inhibitory impurities. While both patents appear to recognize the need to remove undesirable materials, such as starting reactants, reaction by-products, etc., neither contemplates the presence, much less the need to avoid anti-catalysts, i.e., the inhibitory impurities. See, for example, inhibitors as described in Nielsen, U.S. Pat. No. 3,383,356.

In Ashby and Modic it is disclosed that two types of olefinic siloxanes of a very specific nature can be used alone, or in combination, as complexes with platinum to produce superior catalysts, e.g., in the reactions of hydrogenosiloxanes with olefinically unsaturated and/or hydroxylated organic compounds and the reactions of hydrogeno-siloxanes with olefinically unsaturated and/or hydroxyl-substituted organosiloxanes.

It has now been found that the prior art procedures can be modified in such a way that valuable complex catalysts are produced which have extreme activity, improved stability and greater ease in production. While the reasons for these beneficial effects are not clearly understood, it is believed that careful selection of component ratios and methods of forming the complex lead to novel complexes different from any described in the prior art, especially the Willing, the Karstedt, and the Ashby and Modic patents mentioned above.

The features which distinguish the present catalysts are process-related. For example, as will be shown hereinafter, a mixture of chloroplatinic acid and divinyltetramethyldisiloxane reacted according to Willing, Example 1, produces a catalyst with a platinum content of 0.27 weight percent, using a ratio of ingredients (before heating) sufficient to provide 0.0037 gram atoms of platinum per mole of vinyl groups in the disiloxane. If, on the other hand, the process of Karstedt, Example 10, is used, the acid-binding agent, sodium bicarbonate being present prior to heating the ingredients, the platinum content is increased to 4.6 weight percent. In curing tests at the same platinum levels, 10 parts per million (ppm) the catalysts show times to cure of 5.0 hours (Willing) and 1.5 hours (Karstedt), respectively. If, on the other hand, the ratio of gram atoms of platinum to moles of vinyl content is changed from Willing's level, up to at least 0.01:1 and preferably more than 0.02:1, and the catalyst forming reaction is conducted in the substantial absence of an acid binding agent, then catalysts with more than 2.0 percent, but less than 4.0 percent by weight of platinum are produced. Most surprisingly, at 10 ppm of contained platinum, the catalyzed compositions cure in only 1.0 hours, showing improved activity over either Willing or Karstedt. The catalysts are better in terms of storage stability, too, maintaining their initial clarity for longer times, with no tendency to precipitate. The catalysts of this invention in addition to having a lower content of inhibiting impurities are industrially more efficient to make, because of the reduction in volumes used, and avoidance of the need to use acid binding agents.

DESCRIPTION OF THE INVENTION

According to the present invention there are provided platinum-siloxane catalysts, substantially free of inhibitory impurities, and consisting essentially of platinum and an organosiloxane of the formula

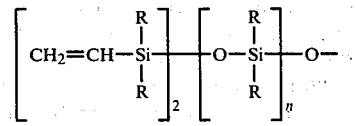

wherein R is free of aliphatic unsaturation and is selected from alkyl radicals, cycloalkyl radicals and phenyl radicals and n is 0 or an integer of from 1 to 1000, said platinum and said organosiloxane having been chemically combined by heating, in the substantial absence of an acid binding agent,
(i) a platinum halide with
(ii) an amount of said organosiloxane sufficient to provide not less than about 0.01 gram atom of platinum per mole of vinyl content in said organosiloxane compound, and an amount of platinum in said catalyst of not substantially less than about 2.0 percent by weight, said heating being carried out for a time sufficient to insure substantially complete reaction therebetween.

In preferred features, R is methyl, and the amount of platinum in the catalyst is within the range of from about 2.0 to about 4.0 percent by weight.

Also contemplated are compositions comprising
(a) an organosilicon compound containing at least one ≡SiH bond;
(b) an organic compound containing an aliphatic unsaturated group, a hydroxyl group, or a mixture of such groups; and
(c) a catalytic amount of a platinum-siloxane complex catalyst, substantially free of inhibitory impurities, and consisting essentially of platinum and an organosiloxane of the formula

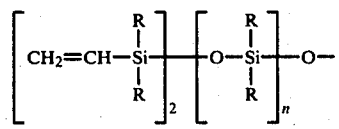

wherein R is free of aliphatic unsaturation and is selected from alkyl radicals, cycloalkyl radicals and phenyl radicals and n is as above defined, said platinum and said organosiloxane having been chemically combined by heating, in the substantial absence of an acid binding agent,
(i) a platinum halide with
(ii) an amount of said organosiloxane sufficient to provide not less than about 0.01 gram atom of platinum per mole of vinyl content in said organosiloxane compound and an amount of platinum in said catalyst of not substantially less than about 2.0 percent by weight, said heating being carried out for a time sufficient to insure substantially complete reaction therebetween.

In preferred features, such compositions will be those in which component (a) is an organohydrogenpolysiloxane; component (b) is an organosilicon compound containing at least one silicon-bonded aliphatic unsaturated group, or an organosilicon compound containing at least one silicon-bonded hydroxyl group; and especially a vinyl-terminated polydimethylsiloxane or a hydroxy-terminated polydimethylsiloxane. In other preferred features, in the composition, in complex catalyst (c), R is methyl; and in said composition in said complex catalyst (c), the amount of platinum is within the range of from about 2.0 to about 4.0 percent by weight. Especially preferably the catalytic amount of said complex catalyst (c) comprises 10 parts by weight per million parts by weight of the composition.

The term "total chloride" used hereinafter will designate chloride that can be detected by the disodium biphenyl procedure as shown in Analytical Chemistry, vol. 22, 311 (1950).

The platinum content of the catalyst compositions is determined by the colorimetric method as described in Analytical Chemistry, vol. 23, 299 (1951).

The term "substantially free of inhibitory impurities" means free of components which extend gel time at approximately room temperature, i.e., 25° C., more than 50% above that which is attainable with complexes comprising platinum and the vinyldisiloxane prepared according to the method described and claimed herein. A convenient way for determing such gel time is to make a master solution in a vinyl-terminated or hydroxyl-terminated polydimethylsiloxane of the catalyst which will contain approximately 100 ppm. of platinum, dilute it to contain 10 ppm as Pt and then to mix this with a liquid organohydrogenpolysiloxane and to measure gel time. If the catalyst is substantially free of inhibitory impurities, it will exhibit a gel time substantially less than that observed with the catalysts of the prior art.

As in the above-mentioned patents, R in the disiloxane can be alkyl, cycloalkyl, or aryl, illustratively containing from 1 to 18 carbon atoms, as the case may be, typically, methyl, ethyl, propyl, butyl, pentyl, hexyl, heptyl, octyl, etc., cyclohexyl, cycloheptyl, etc., phenyl, tolyl, xylyl, etc., benzyl, phenylethyl, phenylpropyl, etc. If R is methyl, the products will be colorless liquids, sensitive to air and/or moisture and soluble in tetrahydrofuran, acetonitrile and hexane.

The catalysts can be prepared by reacting a platinum halide with the disiloxane under conditions of heating followed by isolation of the complex by methods leaving it substantially free of inhibiting impurities, as defined above. Suitable platinum halides are, for example, $H_2PtCl_6.nH_2O$, and metal salts such as $NaHPtCl_6.nH_2O$; $KHPtCl_6.nH_2O$; $Na_2PtCl_6.nH_2O$; $KPtCl_6.nH_2O$. Also $PtCl_4.nH_2O$ and platinous-type halides such as $PtCl_2$; $Na_2PtCl_4.nH_2O$; $H_2PtCl_4.nH_2O$; $NaHPtCl_4.nH_2O$; $KHPtCl_4.nH_2O$; $K_3PtBr_4$, and the like. Furthermore, platinum halide complexes with aliphatic hydrocarbons as disclosed in Ashby U.S. Pat. No. 3,159,601 and 3,159,662 can be used, for example $((CH_2=CH_2).PtCl_2)_2$; $(PtCl_2.C_2H_6)_2$; etc.

In a preferred procedure, an amount of divinyltetramethyldisiloxane sufficient to provide at least about 1 mole of vinyl groups per 0.01 gram atoms of platinum and preferably about 1 mole of vinyl per 0.02 gram atoms of platinum will be added to the platinum halide in a suitable reaction vessel. The mixture is agitated and heated to above 60° C. the exothermic heat of reaction raises it to above 120° C., e.g., 124° C. Heating is maintained at 120° C., for long enough to complete the reaction, usually about 1 hour after gaseous byproducts cease to evolve. Then the mixture is cooled, and filtered. Washing was distilled, deionized water to neutrality is desirable.

In addition to the above-described platinum-siloxane complexes, there are also included in the present invention, reactive compositions having at least 0.01 part, and preferably 1 to 200 parts of platinum per million parts of aliphatically unsaturated and/or hydroxyl-containing organic compound and a ≡SiH containing material. In preferred compositions, the aliphatically unsaturated and/or hydroxyl-containing compound will be an organopolysiloxane, and especially preferably one of the compounds illustrated in this connection in Karstedt, U.S. Pat. No. 3,775,452. Such compositions are cured to the solid state with a variety of silicon hydrides, also as shown in Karstedt, U.S. Pat. No. 3,775,452. Suitable silicon hydrides are, for example, organocyclopolysiloxanes containing at least two chemically combined RHSiO units, and organopolysiloxane polymers having chemically combined (R)Si(H)O units, where R is as above defined. The organopolysiloxane can be a fluid having terminal diorganoalkenylsiloxy units, or terminal diorganohydroxysiloxy units such as dimethylvinylsiloxy units, having a viscosity of at least 50 centipoises at 25° C. In addition, organopolysiloxane gums having a viscosity of at least 100,000 centipoises at 25° C. and chemically combined methylvinylsiloxy and/or hydroxymethyl siloxy units, etc., can provide for elastomeric foaming products. In addition, the platinum containing organopolysiloxane of the present invention can contain from 10 to 300 parts of filler per 100 parts of organopolysiloxane. For example, fillers include, silica, such as fumed silica, nonreinforcing ground quartz, carbon black, and the like.

DESCRIPTION OF THE PREFERRED EMBODIMENTS

In order that those skilled in the art will be better able to practice the invention, the following examples are given by way of illustration and not by way of limitation. All parts are by weight.

EXAMPLE 1

Chloroplatinic acid, $H_2PtCl_6.6H_2O$ (40.00% Pt), 32.0 grams, was weighed into a 500 ml. reaction flask fitted with a reflux condenser, pot thermometer and equipped for magnetic stirring of the flask contents. Then 210 g. of sym-tetramethyldivinyldisiloxane was added. The composition comprises 0.0265 g. atoms of platinum per mole of vinyl content. The slurry was stirred while heating with a mantle. At about 60° C. an exothermic reaction was observed which drove the temperature to 124° C. and a gaseous reaction product (s) was observed. Heating was continued for 1 hour at 120° C. After cooling, the mixture was filtered through filter paper. The filtrate, a clear amber solution, was washed with four 250 mil portions of distilled, deionized water. The final wash water was neutral (pH 7) to test paper. Analysis of the organic layer for total chloride content and for platinum gave 0.43% chloride and 2.20% platinum. From these analyses a molar ratio of chlorine to platinum of 1.07 is calculated, or approximately 1 g. atom of chlorine per gram atom of platinum.

EXAMPLE 2

A mixture of 100 g. of the neutral, washed solution of Example 1 was mixed (by stirring magnetically) with 10 g. of $NaHCO_3$. The mixture was heated at 100° C. for 1 hour, then the solids were filtered from the cooled mixture. The clear, amber filtrate was analyzed as before for total chloride and platinum content. These were 0.23% and 2.4%, respectively. The chloride to platinum ratio was 0.52:1 or approximately 2 g. atoms of platinum per gram atom of chlorine.

COMPARATIVE EXAMPLE 1A

The procedure of Willing, U.S. Pat. No. 3,419,593, Example 1, was carried out. 3.2 g. of chloroplatinic acid ($H_2PtCl_6.6H_2O$) and 150 g. of sym-divinyltetramethyldisiloxane were heated and stirred in a 500 ml. flask for 1 hour at 120° C. The composition comprises 0.00373 g. atom of platinum per mole of vinyl content. The mixture was cooled and diluted with 260 g. of sym-divinyltetramethyldisiloxane. The filtered product was washed to neutrality with four 250 ml. portions of distilled, deionized water. Test paper was used to determine the neutrality. Total chloride content is 0.084% and platinum content to 0.27% by weight.

COMPARATIVE EXAMPLE 2A

The procedure of Karstedt U.S. Pat. No. 3,814,730, Example 10 was followed: Into a suitable vessel was placed 268 parts of sodium bicarbonate (acid-binding agent) and 761 parts of sym-tetramethyldivinylsiloxane. The air in the vessel was displaced with dry nitrogen and a solution of 190 parts of chloroplatinic acid in 381 parts of ethyl alcohol was added at room temperature with stirring. The mixture was heated at 65° C. for 25 minutes under dry nitrogen. The temperature was then reduced to 40° C. and volatiles were stripped from the vessel under vacuum. The temperature was controlled at 40°–45° C. during stripping which was concluded at 45° C. and 5 mm pressure. Then 381 parts of xylene was added to the residue from the stripping step and the slurried mixture was filtered to remove salts. The filtrate was a straw-colored solution. The total chloride was 0.027 weight percent, and the platinum content was 4.6 weight percent.

In order to determine the activity of the catalysts of Examples 1 and 2 and to compare them with the catalysts of the prior art (Karstedt and Willing), master solutions of each catalyst are prepared by adding them in an amount sufficient to provide 100 ppm Pt in a batch of 75 weight percent vinyl-terminated polydimethylsiloxane (3500 cps viscosity at 25° C.) and 25 weight percent of a soluble trimethyl, methylvinyl and $SiO_2$ units-containing organo-siloxane copolymer.

The masters are then used to prepare more dilute solutions in the same batch of 75:25 organopolysiloxane by combining 3 g. of each concentrated master and 27 g. of the polymer batch to give four final solutions, each containing 10 ppm. by weight of platinum. Next, there is added 3 g. of a 50:50 mixture of liquid organohydrogenpolysiloxane and the vinyl-terminated polydimethylsiloxane to the 30 g. solutions described above. The gel times at 25° C. are then measured with the results set forth in the following Table:

TABLE

| COMPARISON OF PLATINUM CATALYSTS | | | | |
|---|---|---|---|---|
| Composition | Platinum Percent (in undiluted catalyst) | Chloride Percent (in undiluted catalyst) | molar ratio Cl/Pt | Activity Test |
| Example 1 | 2.2 | 0.43 | 1.1 | 1.0 hr. |
| Example 2 | 2.4 | 0.23 | 0.52 | 1.0 hr. |
| Comparative Example 1A | 0.27 | 0.084 | 1.7 | 5.0 hr. |
| Comparative Example 2A | 4.6 | 0.027 | 0.03 | 1.5 hr. |

The above table demonstrates the improved activity of the two catalysts of the present invention. In addition, qualitative findings indicate improved stability on storage of the two preparations over both Willing Example 1 and Karstedt Example 10 and also over Ashby and Modic, U.S. Pat. No. 4,288,345; these findings are based on observing a precipitate in the initially clear catalysts on storage at room temperature.

Many variations will suggest themselves to those skilled in this art in light of the above, detailed description. All such obvious modifications are within the full intended scope of the appended claims.

I claim:
1. A storage-stable platinum-siloxane complex catalyst, substantially free of inhibitory impurities, and consisting essentially of platinum and at least one organosiloxane of the formula

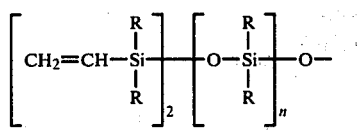

wherein R is free of aliphatic unsaturation and is selected from alkyl radicals, cycloalkyl radicals and phenyl radicals and n is 0 or an integer of from 1 to 1000, said platinum and said organosiloxane having been chemically combined by heating, in the substantial absence of an acid binding agent,
(i) a platinum halide with
(ii) an amount of said organosiloxane sufficient to provide not less than about 0.01 gram atom of platinum per mole of vinyl content in said organosiloxane compound, and an amount of platinum in said catalyst of not substantially less than about 2.0 percent by weight, said heating being carried out for a time sufficient to insure substantially complete reaction therebetween.

2. A complex catalyst as defined in claim 1 wherein R is methyl.

3. A complex catalyst as defined in claim 1 wherein the amount of platinum is within the range of from about 2.0 to about 4.0 percent by weight.

4. A composition comprising
(a) an organosilicon compound containing at least one ≡SiH bond;
(b) an organic compound containing an aliphatic unsaturated group, a hydroxyl group, or a mixture of such groups; and
(c) a catalytic amount of a storage-stable platinum-siloxane complex catalyst,
substantially free of inhibitory impurities, and consisting essentially of
platinum and an organosiloxane of the formula

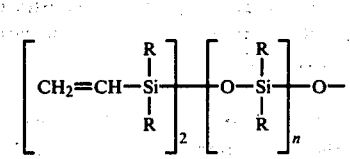

wherein R is free of aliphatic unsaturation and is selected from alkyl radicals, cycloalkyl radicals and phenyl radicals and n is 0 or an integer of from 1 to 1000, said platinum and said organosiloxane having been chemically combined by heating, in the substantial absence of an acid binding agent,
(i) a platinum halide with
(ii) an amount of said organosiloxane sufficient to provide not less than about 0.01 gram atom of platinum per mole of vinyl content in said organosiloxane compound, and an amount of platinum in said catalyst of not substantially less than about 2.0 percent by weight, said heating being carried out for a time sufficient to insure substantially complete reaction therebetween.

5. A composition as defined in claim 4 wherein component (a) is an organohydrogenpolysiloxane.

6. A composition as defined in claim 4 wherein component (b) is an organosilicon compound containing at least one silicon-bonded aliphatic unsaturated group, or an organosilicon compound containing at least one silicon-bonded hydroxyl group.

7. A composition as defined in claim 6 wherein said component (b) comprises a vinyl-terminated polydimethylsiloxane or a hydroxy-terminated polydimethylsiloxane.

8. A composition as defined in claim 4 wherein, in said complex catalyst (c), R is methyl.

9. A composition as defined in claim 4 wherein, in said complex catalyst (c), the amount of platinum is within the range of from about 2.0 to about 4.0 percent by weight.

10. A composition as defined in claim 4 wherein the catalytic amount of said complex catalyst (c) comprises 10 parts by weight per million parts by weight of the composition.

* * * * *